(12) United States Patent
Hillyer

(10) Patent No.: US 8,252,566 B2
(45) Date of Patent: Aug. 28, 2012

(54) ETHANOL PRODUCTION FROM CITRUS WASTE THROUGH LIMONENE REDUCTION

(75) Inventor: Gregory Loyde Hillyer, North Bethesda, MD (US)

(73) Assignee: JJ Florida Properties LLC, Miami, FL (US)

( * ) Notice: Subject to any disclaimer, the term of this patent is extended or adjusted under 35 U.S.C. 154(b) by 506 days.

(21) Appl. No.: 12/468,696

(22) Filed: May 19, 2009

(65) Prior Publication Data

US 2009/0291482 A1  Nov. 26, 2009

Related U.S. Application Data

(60) Provisional application No. 61/054,637, filed on May 20, 2008.

(51) Int. Cl.
C12P 7/06 (2006.01)
C12P 7/08 (2006.01)
C12P 7/10 (2006.01)

(52) U.S. Cl. .......... 435/161; 435/163; 435/165

(58) Field of Classification Search .......... 435/161, 435/163, 165
See application file for complete search history.

(56) References Cited

U.S. PATENT DOCUMENTS

| | | |
|---|---|---|
| 1,781,788 A | 11/1930 | Matzka |
| 2,276,420 A | 3/1942 | Rosenfeld |
| 2,561,072 A | 7/1951 | Reich |
| 2,686,146 A | 8/1954 | Buswell et al. |
| 2,984,601 A | 5/1961 | Sudarsky et al. |
| 3,112,248 A | 11/1963 | Sudarsky et al. |
| 3,845,218 A | 10/1974 | Mussell |
| 3,966,984 A | 6/1976 | Cocke et al. |
| 4,113,573 A | 9/1978 | Gerow |
| 4,291,124 A | 9/1981 | Muller et al. |
| 4,316,956 A | 2/1982 | Lützen |
| 4,403,034 A | 9/1983 | Rogers et al. |
| 4,425,433 A | 1/1984 | Neves |
| 4,488,912 A | 12/1984 | Milch et al. |
| 4,503,079 A | 3/1985 | King et al. |
| 4,547,226 A | 10/1985 | Milch et al. |
| 4,564,595 A | 1/1986 | Neves |
| 4,612,286 A | 9/1986 | Sherman et al. |
| 4,637,835 A | 1/1987 | Nagle |
| 4,650,689 A | 3/1987 | Hedrick |
| 4,818,250 A | 4/1989 | Whitworth |
| 4,915,707 A | 4/1990 | Whitworth |
| 4,952,504 A | 8/1990 | Pavilon |
| 5,061,497 A | 10/1991 | Thacker et al. |
| 5,079,011 A | 1/1992 | Lommi et al. |
| 5,135,861 A | 8/1992 | Pavilon |
| 5,177,008 A | 1/1993 | Kampen |
| 5,177,009 A | 1/1993 | Kampen |
| 5,186,722 A | 2/1993 | Cantrell et al. |
| 5,220,105 A | 6/1993 | Kruger, Jr. et al. |
| 5,252,107 A | 10/1993 | Wilkins, Jr. |
| 5,348,871 A | 9/1994 | Scott et al. |
| 5,354,851 A | 10/1994 | Graves |
| 5,403,612 A | 4/1995 | Huang |
| 5,501,713 A | 3/1996 | Wilkins, Jr. |
| 5,554,520 A | 9/1996 | Fowler et al. |
| 5,607,486 A | 3/1997 | Wilkins, Jr. |
| 5,710,030 A | 1/1998 | Anderson |
| 5,846,787 A | 12/1998 | Ladisch et al. |
| 6,251,643 B1 | 6/2001 | Hansen et al. |
| RE37,629 E | 4/2002 | Wilkins, Jr. |
| 6,509,180 B1 | 1/2003 | Verser et al. |
| 6,569,653 B1 | 5/2003 | Alard et al. |
| 6,703,227 B2 | 3/2004 | Jakel et al. |
| 6,740,508 B2 | 5/2004 | Ulrich et al. |
| 6,962,722 B2 | 11/2005 | Dawley et al. |
| 7,083,954 B2 | 8/2006 | Jakel et al. |
| 7,101,691 B2 | 9/2006 | Kinley et al. |
| 7,102,057 B2 | 9/2006 | Lanahan et al. |
| 7,115,298 B2 | 10/2006 | Keithly et al. |
| 7,138,257 B2 | 11/2006 | Galli et al. |
| 2002/0160469 A1 | 10/2002 | Ingram et al. |
| 2003/0077771 A1 | 4/2003 | Verser et al. |
| 2003/0194788 A1 | 10/2003 | Jakel et al. |
| 2003/0224496 A1 | 12/2003 | Jakel et al. |
| 2004/0091983 A1 | 5/2004 | Veit et al. |
| 2004/0170731 A1 | 9/2004 | Subramaniam et al. |
| 2004/0253696 A1 | 12/2004 | Grichko |
| 2005/0054064 A1 | 3/2005 | Talluri et al. |
| 2005/0118692 A1 | 6/2005 | Kinley et al. |
| 2005/0239181 A1 | 10/2005 | Lewis et al. |
| 2006/0035354 A1 | 2/2006 | Galli et al. |
| 2006/0121589 A1 | 6/2006 | Dunn-Coleman et al. |
| 2006/0127999 A1 | 6/2006 | Verser et al. |
| 2006/0154353 A1 | 7/2006 | Duan et al. |
| 2006/0177916 A1 | 8/2006 | Stewart et al. |
| 2006/0260011 A1 | 11/2006 | Carter et al. |
| 2006/0275882 A1 | 12/2006 | Martinez-Gutierrez et al. |

(Continued)

OTHER PUBLICATIONS

Atsushi Fukuoka et al. "Catalytic Conversion of Cellulose into Sugar Alcohols" Angew. Chem. Int. Ed. 2006, 45, 5161-5163.*

(Continued)

Primary Examiner — Jon P Weber
Assistant Examiner — Thane Underdah
(74) Attorney, Agent, or Firm — Feldman Gale, P.A.; Walter C. Frank

(57) ABSTRACT

The present invention relates to processes for producing ethanol from citrus waste wherein the level of fermentation-inhibiting compounds found in citrus waste or the complex polysaccharide or sugars derived therefrom is reduced using a pre-fermentation treatment step to lower the level of fermentation-inhibiting compounds to the fermentation feedstock.

54 Claims, No Drawings

U.S. PATENT DOCUMENTS

| | | |
|---|---|---|
| 2006/0281157 A1 | 12/2006 | Chotani et al. |
| 2006/0292677 A1 | 12/2006 | Ostrander |
| 2007/0031953 A1 | 2/2007 | Dunson, Jr. et al. |
| 2007/0037267 A1 | 2/2007 | Lewis et al. |
| 2007/0082385 A1 | 4/2007 | Smith et al. |
| 2007/0099278 A1 | 5/2007 | Aare |
| 2007/0134780 A1 | 6/2007 | Grichko |
| 2007/0134781 A1 | 6/2007 | Agblevor |
| 2007/0141688 A1 | 6/2007 | Henderson et al. |
| 2007/0141689 A1 | 6/2007 | Bhargava et al. |
| 2007/0141691 A1 | 6/2007 | Hirl |
| 2007/0155001 A1 | 7/2007 | Veit et al. |
| 2007/0178567 A1 | 8/2007 | Lewis |
| 2007/0178569 A1 | 8/2007 | Leschine et al. |
| 2007/0184541 A1 | 8/2007 | Karl et al. |

OTHER PUBLICATIONS

Wilkins et al. "Ethanol production by *Saccharomyces cerevisiae* and *Kluyveromyces marxianus* in the presence of orange-peel oil" World J Microbiol Biotechnol (2007) 23:1161-1168.*

Grau et al. "Liquid phase hydrogenation, isomerization and dehydrogenation of limonene and derivatives with supported palladium catalysts" Journal of Molecular Catalysis A: Chemical 148 (1999) 203-214.*

Newhall "Derivatives of (+)-Limonene. I. Esters of trans-p-Menthane-1,2-diol" J. Org. Chem., 1958, 23 (9), pp. 1274-1276.*

Robinson et al. "The use of catalytic hydrogenation to intercept carbohydrates in a dilute acid hydrolysis of biomass to e ect a clean separation from lignin" Biomass and Bioenergy 26 (2004) 473-483.*

Abbas, Charles A., Lignocellulosics to ethanol: meeting ethanol demand in the future, The Alcohol Textbook $4^{th}$ Edition, 2003, pp. 41-57, Ch. 5, K.A. Jacques (ed.), T.P. Lyons (ed.), D.R. Kelsall (ed.).

Ben-Shalom, Noach, Hinderance of Hemicellulose and Cellulose Hydrolysis by Pectic Substances, Journal of Food Science, 1986, pp. 720-721; 730, vol. 51, No. 3.

Bothast, R.J., et al., Biotechnological process for conversion of corn into ethanol, Appl Microbiol Biotechnol, 2005, pp. 19-25, vol. 67.

Cameron, Randall, et al., Mapping Demethylated Block Size and Distribution in Pectin from Citrus Processing Waste, Research Project: Enhanced Utilization of Carbohydrates and Polysaccharides from Citrus Processing Waste Streams, USDA Agricultural Research Service, Oct. 21, 2004, Florida.

Cellulose Conversion Key to Fuel of the Future, National Renewable Energy Laboratory, Aug. 1994.

Doran, Joy Bethune, et al., Fermentations of Pectin-Rich Biomass with Recombinant Bacteria to Produce Fuel Ethanol, Applied Biochemistry and Biotechnology, 2000, pp. 141-152, vol. 84-86.

Echeverria, Ed, et al., Effect of Cell Wall Hydrolysis on Brix in Citrus Fruit, Proc. Fla. Stat Hort. Soc., 1988, pp. 150-154, vol. 101.

Flores, Alfredo, Citrus Peel Waste a Potential Source of Ethanol, USDA Agricultural Research Service, Apr. 6, 2006.

Golias, Helen, et al., Characteristics of cellulose preparations affecting the simultaneous saccharification and fermentation of cellulose to ethanol, Biotechnology Letters, 2000, pp. 617-621, No. 22.

Grohmann, K., et al., Fermentation of Galacturonic Acid and Other Sugars in Orange Peel Hydrolysates by the Ethanologenic Strain of *Escherichia coli*, Biotechnology Letters, Mar. 1994, pp. 281-286, vol. 16, No. 3.

Grohmann, K., et al., Fermentation of Sugars in Orange Peel Hydrolysates to Ethanol by Recombinant *Escherichia coli* KO11, Applied Biochemistry and Biotechnology, 1995, pp. 423-435, vol. 51/52.

Grohmann, K., et al., Fractionation and Pretreatment of Orange Peel by Dilute Acid Hydrolysis, Biosource Technology 54, 1995, pp. 129-141, Florida.

Grohmann, K., et al., Hydrolysis of Orange Peel With Pectinase and Cellulase Enzymes, Biotechnology Letters, Dec. 1992, pp. 1169-1174, vol. 14, No. 12.

Grohmann, K., et al., Production of Ethanol from Enzymatically Hydrolyzed Orange Peel by the Yeast *Saccharomyces cerevisiae*, Applied Biochemistry and Biotechnology, 1994, pp. 315-327, vol. 45/46.

How Do We Get d-Limonene and Orange Oil?, What is d-Limonene, http://www.floridachemical.com/whatisd-limonene.htm, retrieved May 15, 2007, p. 2.

Ingledew, W.M., Continuous fermentation in the fuel alcohol industry: How does the technology affect yeast?, The Alcohol Textbook $4^{th}$ Edition, 2003, pp. 135-143, Ch. 11, K.A. Jacques (ed.), T.P. Lyons (ed.), D.R. Kelsall (ed.).

Jacobs, P.B. & H.P. Newton, http://www.journeytoforever.org/bifuel_library/ethanol_motherearth/meCh3.html, U.S. Dept. Agr., Miscl. Publ 327, Dec. 1938, retrieved May 15, 2007.

Kelsall, Dave R., et al., Grain dry milling and cooking procedures: extracting sugars in preparation for fermentation, The Alcohol Textbook $4^{th}$ Edition, 2003, pp. 9-21, Ch. 2, K.A. Jacques (ed.), T.P. Lyons (ed.), D.R. Kelsall (ed.).

Kelsall, Dave R., et al., Practical management of yeast: conversion of sugars to ethanol, The Alcohol Textbook $4^{th}$ Edition, 2003, pp. 121-133, Ch. 10, K.A. Jacques (ed.), T.P. Lyons (ed.), D.R. Kelsall (ed.).

Kesterson, J.W., et al., By-Products and Specialty Products of Florida Citrus, Agricultural Experiment Stations, Institute of Food, University of Florida, Gainesville, Bulletin 784, Dec. 1976, pp. 1-119.

Kling, S.H., et al., Enhancement of Enzymatic Hydrolysis of Sugar Cane Bagasse by Steam Explosion Pretreatment, Biotechnology and Bioengineering, 1987, pp. 1035-1039, vol. XXIX.

Larson, Jim, et al., Managing the Four Ts of cleaning and sanitizing: time, temperature, titration and turbulence, The Alcohol Textbook $4^{th}$ Edition, 2003, pp. 299-318, Ch. 21, K.A. Jacques (ed.), T.P. Lyons (ed.), D.R. Kelsall (ed.).

Luzio, Gary A., Determination of Galacturonic Acid Content of Pectin Using a Microtiter Plate Assay, Proc. Fla. State Hort. Soc., 2004, pp. 416-421, vol. 117, Florida.

Madson, P.W., Ethanol distillation: the fundamentals, The Alcohol Textbook $4^{th}$ Edition, 2003, pp. 319-336, Ch. 22, K.A. Jacques (ed.), T.P. Lyons (ed.), D.R. Kelsall (ed.).

Marshall, M.R., et al., A Comparison of Enzymatic and Lime Treatments for Extraction of Alcohol Soluble Solids from Citrus Peel, Journal of Food Science, 1985, pp. 1211-1212, vol. 50.

McAloon, Andrew, et al., Determining the Cost of Producing Ethanol from Corn Starch and Lignocellulosic Feedstocks, National Renewable Energy Laboratory, pp. 1-30, Appendix, Oct. 2000.

Meredith, John, Understanding energy use and energy users in contemporary ethanol plants, The Alcohol Textbook $4^{th}$ Edition, 2003, pp. 355-361, Ch. 25, K.A. Jacques (ed.), T.P. Lyons (ed.), D.R. Kelsall (ed.).

Narendranath, N.V., Bacterial contamination and control in ethanol production, The Alcohol Textbook $4^{th}$ Edition, 2003, pp. 287-298, Ch. 20, K.A. Jacques (ed.), T.P. Lyons (ed.), D.R. Kelsall (ed.).

Nishio, Naomichi, et al., Production of Macerating Enzymes of Mandarin Orange Peel by Fungal Cultures, European J. Appl. Microbiol. Biotechnology, 1979, pp. 371-378, vol. 6.

Open Hopper Chopper Pump, http://industrial-paints.globelspec.com/FeaturedProducts/Detail/Seepex/Open_Hopper_Chopper_Pump/17 Retrieved May 15, 2007.

Philippidis, George P., et al., Study of the Enzymatic Hydrolysis of Cellulose for Production of Fuel Ethanol by the Simultaneous Saccharification and Fermentation Process, Biotechnology and Bioengineering, 1993, pp. 846-853, vol. 41.

Power, Ronan F., Enzymatic conversion of starch to fermentable sugars, The Alcohol Textbook $4^{th}$ Edition, 2003, pp. 23-32, Ch. 3, K.A. Jacques (ed.), T.P. Lyons (ed.), D.R. Kelsall (ed.).

Production Processes Used to Produce Ethanol and Distiller's Co-Products, Ethanol Production and its Co-Products, pp. 1-8, vol. 11, DDGS Users Handbook, www.grains.org/ddgs-user-handbook, accessed Apr. 19, 2012.

Research Project: Enhanced Utilization of Carbohydrates and Polysaccharides from Citrus Processing Waste Streams, USDA Agricultural Research Service, Retrieved May 15, 2007, Florida.

Russell, Inge, Understanding yeast fundamentals, The Alcohol Textbook $4^{th}$ Edition, 2003, pp. 85-117, Ch. 9, K.A. Jacques (ed.), T.P. Lyons (ed.), D.R. Kelsall (ed.).

Wilkins, Mark, Citrus Peel Ethanol. Florida's Biofuel for the Future, Research Project: Enhanced Utilization of Carbohydrates and Polysaccharides from Citrus Processing Waste Streams, USDA Agricultural Research Service, Oct. 21, 2004, Florida.

Wilkins, Mark R., et al., Effect of Seasonal Variation on Enzymatic Hydrolysis of Valencia Orange Peel Waste, Proc. Fla. State Hort. Soc., 2005, pp. 419-422, vol. 118, Florida.

Wilkins, Mark R., et al., Hydrolysis of grapefruit peel waste and cellulose and pectinase enzymes, Bioresource Technology (2006), doi:10 1016/j.biotech 2006.06.022.

Zhou, Weiyang, et al., Economic analysis of ethanol production from citrus peel waste, Research Project: Enhanced Utilization of Carbohydrates and Polysaccharides from Citrus Processing Waste Streams, USDA Agricultural Research Service, May 10, 2007, Florida.

* cited by examiner

ETHANOL PRODUCTION FROM CITRUS WASTE THROUGH LIMONENE REDUCTION

CROSS REFERENCE TO RELATED APPLICATION

This application claims priority to U.S. Provisional Application Ser. No. 61/054,637, filed May 20, 2008, the entire disclosure of which is incorporated herein by reference in its entirety.

FIELD OF THE INVENTION

The present invention provides processes for producing ethanol from citrus waste wherein the level of fermentation-inhibiting compounds found in citrus waste or the complex polysaccharides or sugars derived therefrom is reduced using a pre-fermentation treatment step to lower the level of fermentation-inhibiting compounds to the fermentation feedstock.

BACKGROUND OF THE INVENTION

Florida produces approximately 5 million tons of orange peel waste each year. Most of this peel waste is dried, pelletized, and sold as beef or milk cattle feed filler commonly referred to as citrus pulp pellets.

High gasoline prices, overdependence on foreign oil, and a continuing demand for renewable energy sources have led to increased research interest in the general field of citrus peel waste conversion, and in particular, to the transformation of peel waste to ethanol. Current processes generally involve hydrolyzing citrus peel comprising a complex mixture of polysaccharides to provide fermentable sugars, fermenting the sugars to produce ethanol, and isolating the ethanol and other by-products.

Unfortunately, some compounds found in citrus peel or produced during the steps converting citrus peel into fermentable sugars act as fermentation inhibitors in the conversion of these sugars to ethanol. Among these compounds, limonene, a terpene-based component in citrus peel, is known to impede fermentation processes (See Grohmann, et al., *Production of Ethanol from Enzymatically Hydrolyzed Orange Peel by the Yeast Saccharomyces Cerevisiae*, Applied Biochemistry and Biotechnology, Vol. 45 (1994)). Limonene is generally understood to provide a natural defense for citrus against bacteria, viruses, molds, and other organisms and to inhibit fermentation by typical processes that would yield ethanol. It has been estimated that, for efficient fermentation, limonene in the citrus peel waste should be below 3000 parts per million and perhaps even below 1500 ppm.

Stewart et al. (US Patent Application No. 2006/0177916) describes a process of producing ethanol from citrus waste where limonene is removed prior to fermentation. The disclosed process includes limonene removal via evaporation and steam stripping from citrus peel, hydrolysis of the limonene-stripped citrus peel waste, and fermentation of the resulting hydrolysis mixture to produce ethanol (or simultaneous hydrolysis and fermentation). The steam-stripped limonene may be recovered by condensation. Stewart does not address the possibility of chemically modifying limonene to reduce or eliminate its fermentation-inhibiting properties.

Cantrall et al. (U.S. Pat. No. 5,186,722) describes that limonene can be used as feedstock for hydrocarbon-based fuels. A variety of products including aromatics (e.g., 1-methyl-4-(1-methylethyl)benzene) and saturated hydrocarbons (e.g., 1-methyl-4-(1-methylethyl)cyclohexane (i.e., menthane)) were produced as mixtures from purified limonene using a hydrogenation catalyst and a variety of other reaction variables (e.g., heat, pressure, and hydrogen). Certain mixtures containing considerable aromatic content were tested and shown to be useful gasoline additives. Cantrall did not specifically test menthane as a gasoline additive. Neither did Cantrall suggest forming menthane in an aqueous mixture of citrus waste, nor the subsequent fermentation of a citrus peel hydrolysate containing certain terpenes that did not substantially inhibit the fermentation. Cantrall also lacks a suggestion that a fermentation beer containing ethanol and certain of these terpenes that do not substantially inhibit the fermentation could be used to provide fuels as an alternative to gasoline.

Inasmuch as there is a continuing demand for alternative and/or renewable energy resources, a need to reduce dependence on foreign oil supplies, and a need to reduce or stabilize gasoline prices for example, there is still an unfulfilled need for a specific and effective solution to address one or more of these issues. In view of the above, it is highly desirable to find new methods of eliminating limonene or other fermentation-inhibiting compounds from citrus waste in order to enhance the production of ethanol therefrom. The present invention is directed to these, as well as other important ends.

SUMMARY OF THE INVENTION

Generally, the present invention is directed in part to novel methods for producing ethanol from citrus waste, which may include a step for reducing or hydrogenating limonene, other unsaturated terpene components, or other fermentation-inhibiting compounds found in citrus waste. Alternatively, the methods may include a step wherein the limonene, other unsaturated terpene components, or other fermentation-inhibiting compounds, are modified to remove or alter certain isolated double bonds in the limonene, other terpene components, or other fermentation-inhibiting compounds.

The present invention is directed in part to methods for producing ethanol from citrus waste, comprising:
  a. fermenting a catalyst-contacted aqueous mixture of fermentable sugars derived from citrus waste to produce an aqueous mixture containing ethanol, wherein the level of at least one compound from the citrus waste capable of inhibiting the fermentation is reduced to provide a second compound that inhibits the fermentation less than the at least one compound, said level reduced by a contacting with hydrogen and a catalyst prior to the fermentation; and
  b. removing the ethanol from the mixture.

In certain embodiments, the present invention provides methods for producing ethanol from citrus waste, comprising:
  a. hydrolyzing an aqueous slurry of citrus waste to yield a mixture of hydrolyzed citrus waste in an aqueous solution (saccharification);
  b. hydrogenating the limonene present in the mixture with a hydrogen source and a catalyst;
  c. fermenting the saccharified and hydrogenated mixture; and,
  d. removing the resulting ethanol from the fermentation mixture.

In certain embodiments, the present invention provides methods for producing ethanol from citrus waste, comprising:
  a. hydrogenating, in the presence of a hydrogen source and a catalyst, the limonene present a slurry of citrus waste to provide a reduced limonene mixture;

b. hydrolyzing the mixture of hydrogenated citrus waste in an aqueous solution (saccharification);
c. fermenting the saccharified and hydrogenated mixture; and,
d. removing the resulting ethanol from the fermentation mixture.

In certain embodiments, the present invention provides methods for producing ethanol from citrus waste, comprising:
a. hydrolyzing an aqueous mixture of citrus waste to provide a fermentable aqueous mixture comprising sugars derived from the citrus waste (saccharification);
b. contacting the mixture of fermentable aqueous sugars with hydrogen and a catalyst;
c. fermenting the aqueous mixture obtained from step (b) to produce an aqueous mixture containing ethanol; and,
d. removing the ethanol from the mixture from step (c).

In certain embodiments, the present invention provides methods for producing ethanol from citrus waste, comprising:
a. contacting an aqueous mixture of citrus waste with hydrogen and a catalyst;
b. hydrolyzing the aqueous mixture of citrus waste from step (a) to provide a fermentable aqueous mixture comprising sugars derived from the citrus waste (saccharification);
c. fermenting the aqueous mixture obtained from step (b) to produce an aqueous mixture containing ethanol; and
d. removing the ethanol from the mixture from step (c).

In certain embodiments, the present invention provides methods for producing ethanol from citrus waste, comprising:
a. contacting a mixture comprising citrus waste containing one or more fermentation-inhibitory compounds with hydrogen and a catalyst to provide a catalyst-contacted citrus waste mixture having a reduced concentration of at least one fermentation-inhibitory compound; and
b. producing ethanol from the contacted citrus waste mixture.

In certain embodiments, the present invention provides methods for producing ethanol from citrus waste, comprising:
a. providing a mixture which comprises citrus waste, wherein the concentration of at least one fermentation-inhibitory compound in the citrus waste has been reduced by contacting the citrus waste with hydrogen and a catalyst; and
b. producing ethanol from the mixture.

In certain embodiments, hydrogenation of limonene in a fermentable aqueous mixture produces one or more derivatives of limonene.

In certain embodiments, the one or more derivatives of limonene are removed from the fermentable aqueous mixture.

In certain embodiments, the one or more derivatives of limonene are removed from a fermented aqueous mixture.

In certain embodiments, the one or more derivatives of limonene are used as a fuel or fuel additive.

In certain embodiments, a derivative of limonene is menthane.

These and other objects, which will become apparent during the following detailed description, have been achieved by the inventors' discovery that reduction, hydrogenation, or modification of certain fermentation-inhibiting compounds within fermentable sugar process streams derived from citrus peel hydrolysis substantially reduces or eliminates inhibition of fermentation caused by terpene compounds from citrus peel, such as limonene.

DETAILED DESCRIPTION OF THE INVENTION

As used herein, the term "citrus" or "citrus fruit" includes all citrus fruits commercially available, preferably those in substantial commercial production, with orange and grapefruit being even more preferred.

As used herein, the term "citrus peel waste" or "citrus waste" or "citrus waste solids" comprises: the peel, segment membranes (pulp), seeds and/or other components of citrus fruit.

As used herein, the term "substantially saccharify" refers to a saccharification process wherein about more than 50%, preferably more than about 60%, more preferably more than about 75%, still more preferably about more than 90%, yet more preferably more than about 95% of the saccharide bonds present in polysaccharides that are capable of saccharification to fermentable sugars have been hydrolyzed. For example, after citrus waste is substantially saccharified, more than 50% of the fermentable sugars bound within the polysaccharide component of citrus waste are available as fermentable sugars.

As used herein, the term "compound capable of inhibiting the fermentation" refers to any compound present in citrus waste and/or its hydrolyzates whose presence in the fermentation step of any of the methods herein disclosed (including SSF) adversely affects the fermentation of sugars derived from citrus waste for the production of ethanol. As used herein, the term "reducing the level of a compound capable of inhibiting the fermentation" refers to any operation that decreases the level of the fermentation-inhibiting compound in any fermentation feedstock but does not require removal of the inhibiting compound to provide the reduced level. Preferred reduced levels include about 90%, preferably 75%, more preferably 50%, still more preferably 25%, yet more preferably 10% of the level of the at least one compound capable of inhibiting the fermentation originally present in the fermentation feedstock, with about 5% or less being even more preferred.

As used herein, the term "fermentation feedstock" refers to any aqueous citrus waste mixture or further modified mixture thereof. Examples include citrus waste, hydrolyzed citrus waste, hydrogenated citrus waste, and the like, and any combinations thereof.

As used herein, the term "catalyst-contacted aqueous mixture of fermentable sugars derived from citrus waste" refers to aqueous mixtures of fermentable sugars wherein the aqueous mixture of sugars, or the citrus waste from which they may be derived, have been contacted by hydrogen and a catalyst. This includes for example aqueous mixtures of fermentable sugars wherein the reductions or modifications of isolated double bonds are carried out prior to, during or subsequent to saccharification, so long as the contacting occurs prior to fermentation of the sugars.

As used herein, the term "catalyst-contacted aqueous mixture of citrus waste" refers to aqueous mixtures of citrus waste (polysaccharides) wherein the contacting with hydrogen and a catalyst is carried out prior to saccharification of the polysaccharides.

As used herein, the term "converting one or more polysaccharides contained in the citrus waste" refers to any process whereby polysaccharides are broken down, or hydrolyzed, at least in part, to fermentable sugar moieties. In certain aspects, the converting is carried out by organisms, such as for example, in a secondary fermentation step. In other aspects, the hydrolysis is carried out by the addition of enzymes (saccharification). Any method known to the skilled artisan for the hydrolysis of polysaccharides into fermentable sugars is contemplated to be within the ambit of the invention.

As used herein, the term "reducing the level of a compound capable of inhibiting the fermentation" and "reducing the level of one or more fermentation-inhibitory compounds" each refer to any operation that decreases the level of the inhibiting compound in any fermentation feedstock but does not require removal of the inhibiting compound to provide the reduced level. Preferred reduced levels include about 90%, preferably about 75%, more preferably about 50%, still more preferably about 25%, yet more preferably about 10% of the level of the at least one compound capable of inhibiting the fermentation originally present in the fermentation feedstock, with about 5% or less being even more preferred.

All references cited herein are incorporated by reference in their entireties.

While not wishing to be bound by theory, it is believed that the unsaturated bonds present in limonene and similar terpene or terpene-like compounds are, at least in part, responsible for inhibiting the fermentation process of citrus waste. Thus, the present invention is based, at least in part, on the expectation that reduction and/or modification of the isolated carbon-carbon double bonds of limonene and/or similar terpene components will produce a citrus waste composition that may be more readily fermented, either simultaneously with or after hydrolysis of the citrus peel polysaccharides.

In certain embodiments, reduction or modification of the isolated carbon-carbon double bonds is carried out after the polysaccharides have been hydrolyzed. In certain embodiments, reduction or modification of the isolated carbon-carbon double bonds is carried out prior to hydrolyzing the polysaccharides, for example, on a mixture, preferably an aqueous mixture, of the citrus peel waste. The modified citrus peel waste mixture may then be hydrolyzed and fermented, simultaneously or separately.

In certain embodiments, the hydrolyzing and fermenting are performed simultaneously through SSF (i.e., simultaneous saccharification-fermentation).

It may be beneficial to reduce (e.g., shred, grind, mill, press, or squeeze) the size of the citrus waste in order to create more surface area for the hydrogenation and saccharification processes and also to allow for easier transport of the waste (e.g., pumping). Thus, in certain other embodiments, the citrus waste is mechanically reduced in size to form particle of less than about 1 inch prior to hydrolysis. Additional examples of useful particle sizes include less than about 0.9, 0.8, 0.7, 0.6, 0.5, 0.4, 0.3, 0.2, and/or 0.1 inches. These particle sizes can be achieved using a variety of machines that are known in the art, including hammer mills and grinding pumps. The particle sizes described herein represent average particle sizes and are not meant to be limiting. For example, in a mixture of ground citrus peel with average diameter of about 0.5 inches, some of the particles will be about 0.5 inches, while others may be greater or less, such that the average diameter of particles is about 0.5 inches.

In order for fermentation to proceed effectively, the complex carbohydrates of the citrus waste should be broken down into simple, fermentable sugars (e.g., glucose, fructose, sucrose, etc.), such as by hydrolysis (or saccharification) of the polysaccharides. Thus, in certain embodiments, hydrolyzing of the citrus peel waste is performed by contacting the citrus waste with at least one enzyme capable of complex carbohydrate (polysaccharide) hydrolysis. A number of enzymes and enzyme classes are known to have this activity, including without limitations, pectinases, hemicellulases, cellulases, and beta-glucosidases. Mixtures of one or more of these enzymes, other enzymes, and/or enzyme classes may also be used. In certain embodiments, it is beneficial to add water to the mixture comprising citrus waste before or during the hydrolytic step for one or more polysaccharides.

In certain embodiments, reduction and/or modification of the isolated carbon-carbon double bonds of limonene and/or similar terpene components chemically reduces the compounds by partially or completely saturating isolated double bonds (i.e., hydrogenation). It is also known that such processes may lead to transformations wherein certain of the terpene molecules are hydrogenated and others are concurrently dehydrogenated using a process commonly referred to as a disproportionation reaction, which substantially converts the isolated double bond containing compound to compounds have conjugated double bonds, aromatic rings, and/or fully saturated hydrocarbon structures. By means of these compound reductions, alterations, and/or modifications, the level of at least one compound capable of inhibiting the fermentation step of any of the disclosed methods is reduced. In certain preferred embodiments, the compound capable of inhibiting fermentation is reduced, altered, and/or modified to a second compound that inhibits the fermentation less than the at least one compound.

Catalysts and the conditions for their use in the hydrogenation step will be readily apparent to one of ordinary skill in the art. By way of general guidance, the catalyst may be a noble metal catalyst (e.g., Raney Ni, Pd, Pt, Rh, etc.), their various oxides, borides, or other derivatives, or combination thereof. While homogeneous or soluble catalysts may be employed, heterogeneous catalysts are typically employed for at least their ease of separation from the hydrogenation mixture. In other embodiments, the heterogeneous catalyst may be provided on a support to further simplify removal of the catalyst or modify catalyst activity, and the like. Exemplary supports include activated carbon, alumina, zeolites, polymeric supports, as well as numerous other supports known to skilled artisans. In certain embodiments, the supported catalyst is a noble metal catalyst, or combination thereof, preferably selected from Pd/C and Pt/C, and preferably at weight percent of loadings of noble metal on support, for example, from about 1 to about 20%, preferably from about 1 to about 10%, with from about 1 to about 5% being even more preferred, and all combinations and sub-combinations thereof. Other types of catalysts include mixed metal, metal-containing zeolites, and oganometallics. After hydrogenation, the catalyst is optionally removed (e.g., filtered if not on a support) prior to fermentation (or prior to hydrolysis if hydrogenation is performed before hydrolysis).

The level of catalyst or catalyst on support is not typically critical, and any level may be used that catalyzes the desired hydrogenation. In general, a balance is achieved by incorporating a level of catalyst that provides an acceptable rate of hydrogenation given the particular cost, time, temperature, pressure, and/or other reaction/reactor considerations. By way of example, a feedstock having about 1 mole of terpene or similar fermentation-inhibiting material contained therein may be contacted with about 0.005 to about 1 millimoles of noble metal (contained in a catalyst), preferably about 0.005 to about 0.5, still more preferably about 0.05 to about 0.25 millimoles of noble metal contained in the catalyst, and all combinations and subcombinations thereof. Higher and/or lower levels of catalyst may also be employed dependent on the particular feed and the activity of the catalyst, for example.

The hydrogen source is typically hydrogen gas which may be introduced to the mixture in a variety of ways including through surface contact (e.g., the head space in the reaction vessel is substantially hydrogen) or bubbling (e.g., hydrogen is injected directly into the mixture). In alternative embodiments, the hydrogen is generated in situ, such as by disproportionation of compounds already present in the process stream.

The conditions chosen for reduction and/or modification of the isolated carbon-carbon double bonds of limonene and/or similar terpene components will depend on the size of the system and the desired product. By varying the temperature (from about ambient to about 100° C.) and pressure (from about atmospheric to about 2000 psi), the yield and products obtained can be altered.

When ranges are used herein for physical properties of compounds, or reaction conditions, such as the molar ratios of catalysts to reactants, temperatures and/or reaction pressures, all combinations and subcombinations of ranges and specific embodiments therein are intended to be included.

Typically, menthane (1-methyl-4-(1-methylethyl)cyclohexane) is the desired product of reduction and/or modification of the isolated carbon-carbon double bonds of limonene and/or similar terpene components. Of course, other reduced, modified or derivative compounds may result during the hydrogenation and may depend on the conditions, reaction times, types and amounts of catalyst, etc. As noted above, it is expected that menthane or other limonene derivatives lacking the unsaturated double bonds of limonene should not interfere with fermentation. With a boiling point near 171° C., menthane, as well as any other reduced or modified compounds present with similar physical properties, may be distillably removed from the reaction mixture. Since ethanol has a boiling point of 78.5° C., it may be desirable or advisable in some instances to separate the ethanol and menthane at different points in the process or through the use of fractional distillation. Generally speaking, the menthane or other limonene derivatives may be removed prior to or after fermentation. Since menthane is a 10-carbon, fully saturated hydrocarbon (a cyclohexane derivative), it is expected to be capable of combusting within an internal combustion engine. Thus, the menthane or other limonene derivatives recovered from the present process may be useful as a fuel additive or as a fuel itself. In certain applications, such fuels or fuel additives may provide power in whole or in part for the citrus to ethanol process. Accordingly, the present invention contemplates recovery of ethanol and menthane (or other derivatives), separately (at various points in the process) or together (in various ratios) to be used for various reasons (as a fuel, a fuel additive, or as admixtures).

In certain embodiments, the reduction, alteration, and/or modification of the isolated carbon-carbon double bonds of limonene, similar terpene components, or other compounds capable of inhibiting the fermentation step of any of the methods herein disclosed reduces the level of the at least one compound capable of inhibiting the fermentation preferably to below about 3000 parts per million, more preferably below about 2500, more preferably about 2000, more preferably about 1500, with below about 1000 ppm being even more preferred. It should be noted that complete removal of these materials is expected to be difficult and in some instances unnecessary. Therefore, while substantially all of the limonene, related terpenes, and/or other fermentation inhibiting compounds may be removed in some embodiments, residual limonene, and/or other fermentation inhibiting compounds (for example, from about 10 to about 500 ppm) may still remain after reduction, alteration, and/or modification of the isolated carbon-carbon double bonds, for example, hydrogenation.

In certain embodiments, fermenting is performed by contacting any monosaccharides provided by conversion of one or more polysaccharides into fermentable sugars with an ethanol producing organism selected from a yeast, bacteria, or fungi. Non-limiting examples of suitable organisms include brewer's yeast, S. cerevisiae, and E. coli strain KO11. In some embodiments, the polysaccharides are contacted with hydrogen and a catalyst prior to their conversion into fermentable sugars. In other embodiments, the polysaccharides are first converted into fermentable sugars and subsequently contacted with hydrogen and a catalyst. Typically, one or more polysaccharides in the citrus waste are converted into fermentable sugars by a secondary fermentation or a saccharification process, but any known polysaccharide hydrolysis may be employed. The pH and temperature of the mixture may be adjusted to best suit the selected organism as will be appreciated by the skilled artisan. In certain embodiments, water or additional water, if water is already present in the citrus waste mixture, may be added to the citrus waste mixture to facilitate its hydrolysis. As noted above, in other embodiments, the fermentations may be performed simultaneously with a saccharification, a process known as "SSF" (simultaneous saccharification and fermentation). In such situations, the hydrogenation is preferably performed prior to the SSF step.

In certain embodiments, the ethanol formed by fermentation is removed by distillation. This distillation may be run continuously or semi-continuously by removing a portion of the fermentation mixture (e.g., the beer), distilling, and then returning the remaining portion to the fermentation reaction. The distillation may also be performed in batch or semi-batch mode on the entire fermentation reaction mixture. If menthane or other limonene derivatives are present in the fermentation mixture, they too may be removed by distillation. In order to separate the ethanol and menthane if they are separated from the fermentation mixture together, and if desired, a variety of methods may be used, including fractional distillation.

The present invention may be embodied in other specific forms without departing from the spirit or essential attributes thereof. This invention encompasses all combinations and subcombinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

The examples provided are non-inclusive unless otherwise stated. They include but are not limited to the recited examples.

Other features of the invention will become apparent in the course of the following descriptions of prophetic exemplary embodiments that are given for illustration of the invention and are not intended to be limiting thereof.

EXAMPLES

Example 1

Simultaneous Saccharification and Fermentation (SSF)

Aqueous raw citrus waste slurry is ground to achieve a particle size of less than one half inch using a hammer mill. A progressing cavity pump is used to transfer the ground waste slurry to a fermentation mixing tank. To this tank is introduced 5% Pd/C, and hydrogen is then bubbled through the slurry. The slurry is mixed for a time and at a temperature sufficient to hydrogenate the limonene to a level below 3000 ppm. The catalyst is removed by filtration, and the pH of the mixture is measured to determine if adjustment is necessary before addition of saccharification enzymes. Saccharification enzymes are added, followed by ethanol-producing *E. coli* KO11. The contents of the tank are mixed until a sufficient level of ethanol is achieved. The beer is filtered into a distillation tank. Ethanol and menthane are fractionally distilled from the liquid. The solids from fermentation tank are dried for cattle feed.

Example 2

Aqueous raw citrus waste slurry is ground to achieve a particle size of less than one half inch using a hammer mill. A progressing cavity pump is used to transfer the ground waste slurry to a fermentation mixing tank. The pH of the mixture is measured to determine if adjustment is necessary before addition of saccharification enzymes, and adjustment with typical pH adjusting compounds is made, if necessary. The saccharification enzyme(s) is (are) added, and the reaction mixture in the tank is mixed to allow for hydrolysis. 5% Pd/C is added and hydrogen bubbled through the hydrolyzed slurry. The slurry is mixed for a time and at a temperature sufficient to hydrogenate the limonene to a level below 3000 ppm. The solid support is removed, and the pH of the mixture is measured to determine if adjustment is necessary before addition of the fermentation yeasts, and adjustment with typical pH adjusting compounds is made, if necessary. *E. coli* KO11 is added. The contents of the tank are mixed until a sufficient level of ethanol is achieved. The beer is filtered into a distillation tank. Ethanol and menthane are fractionally distilled from the liquid (filtered beer). The solids from the fermentation tank are dried and may be further processed for cattle feed.

Numerous modifications and variations of the present invention are possible in light of the above teachings. It is therefore to be understood that within the scope of the appended claims, the invention may be practiced otherwise that as specifically described herein.

[Embodiment 1] A method for producing ethanol from citrus waste, comprising:
  a. fermenting a catalyst-contacted aqueous mixture of fermentable sugars derived from citrus waste to produce an aqueous mixture containing ethanol, wherein the level of at least one compound from the citrus waste capable of inhibiting the fermentation is reduced to provide a second compound that inhibits the fermentation less than the at least one compound, said level reduced by a contacting with hydrogen and a catalyst prior to the fermentation; and
  b. removing the ethanol from the mixture.

[Embodiment 2] The method of embodiment 1, further comprising hydrolyzing an aqueous mixture of citrus waste to provide a fermentable aqueous mixture comprising sugars derived from the citrus waste (saccharification); and contacting the mixture of fermentable aqueous sugars with hydrogen and a catalyst; to provide the catalyst-contacted aqueous mixture of fermentable sugars derived from citrus waste for fermenting.

[Embodiment 3] The method of embodiment 1, further comprising contacting an aqueous mixture of citrus waste with hydrogen and a catalyst; and hydrolyzing (saccharifying) the catalyst-contacted aqueous mixture of citrus waste; to provide the catalyst-contacted aqueous mixture of fermentable sugars derived from citrus waste for fermenting.

[Embodiment 4] The method of embodiment 2 or 3, further comprising providing the citrus waste in the form of particles with an average particle size of less than about 1 inch.

[Embodiment 5] The method of embodiment 2 or 3, wherein the average particle size of the citrus waste is less than about 0.5 inches.

[Embodiment 6] The method of embodiment 2 or 3, wherein the average particle size of the citrus waste is less than about 0.1 inches.

[Embodiment 7] The method of embodiment 2, 3, 4, 5, or 6, wherein the providing comprises milling or grinding.

[Embodiment 8] The method of embodiment 2, 3, 4, 5, 6 or 7, wherein the citrus waste is contacted with at least one enzyme capable of complex carbohydrate hydrolysis to substantially saccharify the polysaccharides contained in the citrus waste.

[Embodiment 9] The method of embodiment 2, 3, 4, 5, 6, 7 or 8, wherein the enzyme is selected from a pectinase, a hemicellulase, a cellulase, and a beta-glucosidase, or combination thereof.

[Embodiment 10] The method of embodiment 2, 3, 4, 5, 6, 7, 8 or 9, wherein the contacting with hydrogen and the catalyst reduces the level of at least one compound capable of inhibiting the fermentation.

[Embodiment 11] The method of embodiment 2, 3, 4, 5, 6, 7, 8, 9 or 10, wherein substantially all of the at least one compound capable of inhibiting the fermentation is reduced to a second compound that inhibits the fermentation less than the at least one compound.

[Embodiment 12] The method of embodiment 2, 3, 4, 5, 6, 7, 8, 9 or 10, wherein the contacting with hydrogen and the catalyst reduces the presence of the at least one compound capable of inhibiting the fermentation to below about 3000 parts per million.

[Embodiment 13] The method of embodiment 2, 3, 4, 5, 6, 7, 8, 9 or 10, wherein the contacting with hydrogen and the catalyst reduces the presence of the at least one compound capable of inhibiting the fermentation to below about 1500 parts per million.

[Embodiment 14] The method of embodiment 2, 3, 4, 5, 6, 7, 8, 9, 10, 11, 12 or 13, wherein the catalyst is removed prior to fermentation.

[Embodiment 15] The method of embodiment 2, 3, 4, 5, 6, 7, 8, 9, 10, 11, 12 or 13, wherein the at least one compound is limonene and the second compound is menthane.

[Embodiment 16] The method of embodiment 2, 3, 4, 5, 6, 7, 8, 9, 10, 11, 12, 13, 14 or 15, wherein the catalyst is a noble metal catalyst.

[Embodiment 17] The method of embodiment 2, 3, 4, 5, 6, 7, 8, 9, 10, 11, 12, 13, 14, 15 or 16, wherein the catalyst is selected from Pd/C and Pt/C.

[Embodiment 18] The method of embodiment 2, 3, 4, 5, 6, 7, 8, 9, 10, 11, 12, 13, 14, 15, 16 or 17, wherein the catalyst is Pd/C, having from about 1% to about 5% Pd by weight relative to the weight of C in the catalyst.

[Embodiment 19] The method of embodiment 2, 3, 4, 5, 6, 7, 8, 9, 10, 11, 12, 13, 14, 15, 16, 17 or 18, wherein the catalyst is a solid supported catalyst.

[Embodiment 20] The method of embodiment 2, 3, 4, 5, 6, 7, 8, 9, 10, 11, 12, 13, 14, 15, 16, 17, 18 or 19, wherein the fermenting comprises fermenting the catalyst-contacted mixture of fermentable sugars derived from citrus waste with an ethanol producing organism selected from yeast, bacteria, or fungi.

[Embodiment 21] The method of embodiment 20, wherein the ethanol producing organism is selected from brewer's yeast, *S. cerevisiae*, and *E. coli* strain KO11.

[Embodiment 22] The method of embodiment 21, wherein the ethanol producing organism is *E. coli* strain KO11.

[Embodiment 24] The method of embodiment 2, 3, 4, 5, 6, 7, 8, 9, 10, 11, 12, 13, 14, 15, 16, 17, 18, 19, 20, 21 or 22, wherein the hydrolyzing and fermenting are performed simultaneously.

[Embodiment 23] The method of embodiment 15, wherein the ethanol and menthane are separately removed via fractional distillation.

[Embodiment 25] The method of embodiment 15, wherein the menthane is removed via distillation.

[Embodiment 26] The method of embodiment 1, 2, 3, 4, 5, 6, 7, 8, 9, 10, 11, 12, 13, 14, 15, 16, 17, 18, 19, 20, 21, 22, 23, 24 or 25, wherein the ethanol produced by the fermenting is removed by distillation.

[Embodiment 27] The method of embodiment 1, 2, 3, 4, 5, 6, 7, 8, 9, 10, 11, 12, 13, 14, 15, 16, 17, 18, 19, 20, 21, 22, 23, 24, 25 or 26, wherein the citrus waste is derived from orange or grapefruit peel.

[Embodiment 28] A method for producing ethanol from citrus waste, comprising:
 a. contacting a mixture comprising citrus waste containing one or more fermentation-inhibitory compounds with hydrogen and a catalyst to provide a catalyst-contacted citrus waste mixture having a reduced concentration of at least one fermentation-inhibitory compound; and
 b. producing ethanol from the contacted citrus waste mixture.

[Embodiment 29] A method of embodiment 28, wherein the citrus waste is derived from orange or grapefruit peel.

[Embodiment 30] A method of embodiment 28 or 29, further comprising providing the citrus waste in step (a) in the form of particles with an average particle size of less than about 0.5 inches.

[Embodiment 31] A method of embodiment 30, wherein the average particle size of the citrus waste is less than about 0.1 inches.

[Embodiment 32] A method of embodiment 30 wherein the particles are prepared by a method which comprises milling or grinding.

[Embodiment 33] A method of embodiment 28, 29, 30, 31, or 32, wherein the contacting with hydrogen and a catalyst reduces the concentration of at least one of the fermentation-inhibitory compounds in the citrus waste to a level below about 3000 parts per million based on the weight of citrus waste in the mixture from step (a).

[Embodiment 34] A method of embodiment 33, wherein the contacting with hydrogen and a catalyst reduces the concentration of at least one of the fermentation-inhibitory compounds in the citrus waste to a level below about 1500 parts per million.

[Embodiment 35] A method of embodiment 28, 29, 30, 31, 32, 33, or 34, wherein the ethanol is produced in step (b) by a process comprising fermenting the catalyst-contacted citrus waste mixture.

[Embodiment 36] A method of embodiment 35, wherein the fermenting is performed by contacting the catalyst-contacted citrus waste mixture with an ethanol producing organism selected from a yeast, bacteria, and fungi.

[Embodiment 37] A method of embodiment 36, wherein the organism is selected from brewer's yeast, *S. cerevisiae*, and *E. coli* strain KO11.

[Embodiment 38] A method of embodiment 36 or 37, wherein the organism is *E. coli* strain KO11.

[Embodiment 39] A method of embodiment 35, 36, 37, or 38, further comprising isolating the ethanol from the fermented mixture.

[Embodiment 40] A method of embodiment 39, wherein the ethanol is isolated by distillation.

[Embodiment 41] A method of embodiment 35, wherein the fermentation process comprises:
 i. converting one or more polysaccharides contained in the citrus waste into fermentable sugars; and
 ii. fermenting the sugars to produce ethanol.

[Embodiment 42] A method of embodiment 41, wherein step (i) comprises saccharifying the polysaccharides.

[Embodiment 43] A method of embodiment 42, wherein step (i) further comprises adding water to the mixture prior to saccharification.

[Embodiment 44] A method of embodiment 41, 42, or 43, wherein the one or more polysaccharides contained in the citrus waste are contacted with at least one enzyme capable of complex carbohydrate hydrolysis to substantially saccharify the polysaccharides.

[Embodiment 45] A method of embodiment 44, wherein the at least one enzyme is selected from the group consisting of pectinase, hemicellulase, cellulase, and beta-glucosidase, or combination thereof.

[Embodiment 46] A method of embodiment 42, 43, 44, or 45, wherein the saccharifying and the fermenting are performed substantially simultaneously.

[Embodiment 47] A method of embodiment 28, 29, 30, 31, 32, 33, or 34, wherein one or more polysaccharides contained in the citrus waste are converted into fermentable sugars prior to the contacting with hydrogen and a catalyst in step (a).

[Embodiment 48] A method of embodiment 47, wherein the converting comprises saccharifying the polysaccharides.

[Embodiment 49] A method of embodiment 48, wherein the converting further comprises adding water to the mixture prior to saccharification.

[Embodiment 50] A method of embodiment 49, wherein the one or more polysaccharides contained in the citrus waste are contacted with at least one enzyme capable of complex carbohydrate hydrolysis to substantially saccharify the polysaccharides.

[Embodiment 51] A method of embodiment 50, wherein the at least one enzyme is selected from the group consisting of pectinase, hemicellulase, cellulase, and beta-glucosidase, or combination thereof.

[Embodiment 52] A method of embodiment 29, wherein one of the one or more fermentation-inhibitory compounds is limonene.

[Embodiment 53] A method for producing ethanol from citrus waste, comprising:
 a. providing a mixture which comprises citrus waste, wherein the concentration of at least one fermentation-inhibitory compound in the citrus waste has been reduced by contacting the citrus waste with hydrogen and a catalyst; and
 b. producing ethanol from the mixture.

What is claimed is:
1. A method for producing ethanol from citrus waste, comprising:
 a. hydrolyzing an aqueous mixture of citrus waste to provide a fermentable aqueous mixture comprising sugars derived from the citrus waste (saccharification);
 b. contacting the mixture of fermentable aqueous sugars with hydrogen and a hydrogenation catalyst in amounts sufficient to reduce the level of fermentation inhibiting compounds in the mixture;

c. fermenting the aqueous mixture obtained from step (b) to produce an aqueous mixture containing ethanol; and
d. removing the ethanol from the mixture from step (c)
wherein at least one of the fermentation inhibiting compounds comprises limonene.

2. The method of claim 1, wherein the hydrogenation catalyst is a noble metal catalyst.

3. The method of claim 2, wherein the hydrogenation catalyst is Pd/C and Pt/C.

4. The method of claim 3, wherein the hydrogenation catalyst is Pd/C, having from about 1% to about 5% Pd by weight relative to the weight of C in the catalyst.

5. The method of claim 1, further comprising providing the citrus waste in the form of particles with an average particle size of less than about 1 inch.

6. The method of claim 5, wherein the average particle size of the citrus waste is less than about 0.5 inches.

7. The method of claim 5, wherein the providing comprises milling or grinding.

8. The method of claim 1, wherein the citrus waste is contacted with at least one enzyme capable of complex carbohydrate hydrolysis to substantially saccharify the polysaccharides contained in the citrus waste.

9. The method of claim 8, wherein the enzyme is selected from a pectinase, a hemicellulase, a cellulase, and a beta-glucosidase, or combination thereof.

10. The method of claim 1, wherein the citrus waste is derived from orange or grapefruit peel.

11. The method of claim 1, wherein substantially all of at least one of the fermentation inhibiting compounds is reduced to a second compound that inhibits the fermentation less than the at least one compound.

12. The method of claim 11, wherein at least one fermentation inhibiting compound is limonene and the second compound is menthane.

13. The method of claim 12, wherein the menthane is removed via distillation.

14. The method of claim 12, wherein the ethanol and menthane are separately removed via fractional distillation.

15. The method of claim 1, wherein the contacting with hydrogen and the hydrogenation catalyst reduces the concentration of at least one fermentation inhibiting compound to below about 3000 parts per million.

16. The method of claim 15, wherein the contacting with hydrogen and the hydrogenation catalyst reduces the concentration of at least one fermentation inhibiting compound to below about 1500 parts per million.

17. The method of claim 1, wherein the hydrogenation catalyst is removed prior to fermentation.

18. The method of claim 1, wherein the hydrogenation catalyst is a solid support catalyst.

19. The method of claim 1, wherein the fermenting comprises fermenting the catalyst contacted mixture of fermentable sugars derived from citrus waste with an ethanol producing organism selected from yeast, bacteria, or fungi.

20. The method of claim 19, wherein the ethanol producing organism is selected from brewer's yeast, *S. cerevisiae*, and *E. coli* strain KO11.

21. The method of claim 20, wherein the ethanol producing organism is *E. coli* strain KO11.

22. The method of claim 1, wherein the ethanol produced by the fermenting is removed by distillation.

23. A method for producing ethanol from citrus waste, comprising:

a) contacting an aqueous mixture of citrus waste with hydrogen and a hydrogenation catalyst in amounts sufficient to reduce the level of fermentation inhibiting compounds in the mixture;
b) hydrolyzing the aqueous mixture of citrus waste from step (a) to provide a fermentable aqueous mixture comprising sugars derived from the citrus waste (saccharification);
c) fermenting the aqueous mixture obtained from step (b) to produce an aqueous mixture containing ethanol; and
d) removing the ethanol from the mixture from step (c)
wherein at least one of the fermentation inhibiting compounds comprises limonene.

24. The method of claim 23, wherein the hydrolyzing and fermenting are performed simultaneously.

25. The method of claim 24, wherein the citrus waste is derived from orange or grapefruit peel.

26. The method of claim 23, wherein substantially all of at least one of the fermentation inhibiting compounds is reduced to a second compound that inhibits the fermentation less than the at least one compound.

27. The method of claim 26, wherein the hydrogenation catalyst is removed prior to fermentation.

28. The method of claim 26, wherein at least one fermentation inhibiting compound is limonene and the second compound is menthane.

29. A method for producing ethanol from citrus waste, comprising:
a) contacting a mixture comprising citrus waste containing one or more fermentation inhibiting compounds with hydrogen and a hydrogenation catalyst in amounts sufficient to provide a catalyst contacted citrus waste mixture having a reduced concentration of at least one fermentation inhibiting compound; and
b) producing ethanol from the contacted citrus waste mixture
wherein at least one of the fermentation inhibiting compounds comprises limonene.

30. A method of claim 29, wherein the ethanol is produced in step (b) by a process comprising fermenting the catalyst-contacted citrus waste mixture.

31. A method of claim 30, wherein the fermentation process comprises:
i. converting one or more polysaccharides contained in the citrus waste into fermentable sugars; and
ii. fermenting the sugars to produce ethanol.

32. A method of claim 31, wherein step (i) comprises saccharifying the polysaccharides.

33. A method of claim 32, wherein step (i) further comprises adding water to the mixture prior to saccharification.

34. A method of claim 33, wherein the one or more polysaccharides contained in the citrus waste are contacted with at least one enzyme capable of complex carbohydrate hydrolysis to substantially saccharify the polysaccharides.

35. A method of claim 34, wherein the at least one enzyme is selected from the group consisting of pectinase, hemicellulase, cellulase, and beta-glucosidase, or combination thereof.

36. A method of claim 32, wherein the saccharifying and the fermenting are performed substantially simultaneously.

37. A method of claim 30, wherein the fermenting is performed by contacting the catalyst-contacted citrus waste mixture from step (b) with an ethanol producing organism selected from a yeast, bacteria, and fungi.

38. A method of claim 37, wherein the organism is selected from brewer's yeast, *S. cerevisiae*, and *E. coli* strain KO11.

39. A method of claim 38, wherein the organism is *E. coli* strain KO11.

40. A method of claim 30, further comprising isolating the ethanol from the fermented mixture.

41. A method of claim 40, wherein the ethanol is isolated by distillation.

42. A method of claim 29, wherein the citrus waste is derived from orange or grapefruit peel.

43. A method of claim 29, further comprising providing the citrus waste in step (a) in the form of particles with an average particle size of less than about 0.5 inches.

44. A method of claim 43, wherein the average particle size of the citrus waste is less than about 0.1 inches.

45. A method of claim 43 wherein the particles are prepared by a method which comprises milling or grinding.

46. A method of claim 29, wherein the contacting with hydrogen and a hydrogenation catalyst reduces the concentration of at least one of the fermentation inhibiting compounds in the citrus waste to a level below about 3000 parts per million based on the weight of citrus waste in the mixture from step (a).

47. A method of claim 46, wherein the contacting with hydrogen and a hydrogenation catalyst reduces the concentration of at least one of fermentation inhibiting compounds in the citrus waste to a level below about 1500 parts per million.

48. A method of claim 29, wherein one or more polysaccharides contained in the citrus waste are converted into fermentable sugars prior to the contacting with hydrogen and a hydrogenation catalyst in step (a).

49. A method of claim 48, wherein the converting comprises saccharifying the polysaccharides.

50. A method of claim 49, wherein the converting further comprises adding water to the mixture prior to saccharification.

51. A method of claim 50, wherein the one or more polysaccharides contained in the citrus waste are contacted with at least one enzyme capable of complex carbohydrate hydrolysis to substantially saccharify the polysaccharides.

52. A method of claim 51, wherein the at least one enzyme is selected from the group consisting of pectinase, hemicellulase, cellulase, and beta-glucosidase, or combination thereof.

53. A method of claim 50, further comprising removing at least a portion of the water from the converted citrus waste prior to the contacting with hydrogen and a hydrogenation catalyst.

54. A method for producing ethanol from citrus waste, comprising:
   a) providing a mixture which comprises citrus waste, wherein the concentration of at least one fermentation inhibiting compound in the citrus waste has been reduced by contacting the citrus waste with hydrogen and a hydrogenation catalyst; and
   b) producing ethanol from the mixture
   wherein at least one of the fermentation inhibiting compounds comprises limonene.

* * * * *